US006550419B2

(12) United States Patent
Cohen et al.

(10) Patent No.: US 6,550,419 B2
(45) Date of Patent: Apr. 22, 2003

(54) ARTHROPOD DIET DELIVERY SYSTEM

(75) Inventors: Allen C. Cohen, Starkville, MS (US); Rebecca A. Smith, Plano, TX (US); Daniel K. Harsh, Louisville, MS (US)

(73) Assignee: The United States of America as represented by the Secretary of Agriculture, Washington, DC (US)

( * ) Notice: Subject to any disclaimer, the term of this patent is extended or adjusted under 35 U.S.C. 154(b) by 49 days.

(21) Appl. No.: 09/944,343

(22) Filed: Aug. 30, 2001

(65) Prior Publication Data

US 2003/0047142 A1 Mar. 13, 2003

(51) Int. Cl.[7] ............................................. A01K 29/00
(52) U.S. Cl. ........................................................ 119/6.5
(58) Field of Search ................................. 119/51.01, 71, 119/6.5, 6.6, 475, 270; 435/1.1, 348; 426/2, 106

(56) References Cited

U.S. PATENT DOCUMENTS

| 4,418,647 | A | 12/1983 | Hoffman |
| 5,799,607 | A | 9/1998 | Greany et al. |
| 5,834,177 | A | 11/1998 | Cohen |
| 5,945,271 | A | 8/1999 | Cohen |
| 6,235,528 | B1 | 5/2001 | Cohen |

OTHER PUBLICATIONS

J.E. Carpenter and P.D. Greany, Comparative Development and Performance of Artificially Reared versus Host–Reared *Diapetimorpha introita* (Cresson) (Hymenoptera: Ichneumonidae) Wasps, *Biological Control* (1998) 11:203–208.

A. C. Cohen and R. T. Staten, "Long–Term Culturing and Quality Assessment of Predatory Big–Eyed Bugs, *Geocoris Punctipes*," In: *Applications of Genetics to Arthropods of Biological Control Significance,* Eds. S. K. Narang et al., CRC Press, Inc., (1994) Chapter 7, pp. 121–132.

A.C. Cohen and L.K. Smith, "A New Concept in Artificial Diets for *Chrysoperla rufilabris*: The Efficacy of Solid Diets," *Biological Control* (1998) 13:49–54.

A.C. Cohen and N. M. Urias, "Food Utilization and Egestion Rates of the Predator *Geocoris Punctipes* (Hemiptera: Heteroptera) Fed Artificial Diets with Rutin," *J. Entomol. Sci.* (1988) 23(2):174–179.

A.C. Cohen, "Simple Method for Rearing the Insect Predator *Geocoris punctipes* (Heteroptera: Lygaeidae) on a Meat Diet," *Journal of Economic Entomology* (1985) 78(5):1173–1175.

A.C. Cohen, "Improved Method of Encapsulating Artificial Diet for Rearing Predators of Harmful Insects," *Journal of Economic Entomology* (1983) 76(4):957–959.

(List continued on next page.)

*Primary Examiner*—Charles T. Jordan
*Assistant Examiner*—John W. Zerr

(57) ABSTRACT

The present invention is directed to an improved system for the packaging, presentation, and delivery of a semi-solid arthropod diet, for the feeding or oviposition of arthropods. The arthropod diet delivery system of the invention has a diet-filled reservoir covered with a stretchable membrane, wherein the reservoir membrane has a plurality of stretched, thinned outwardly projecting areas thereon (feeding protrusions) which are filled with the semi-solid diet. The interior of a protrusion is in fluid communication with the diet-filled reservoir. The arthropod diet delivery system may optionally further include stretched, thinned inwardly projecting areas in the stretchable reservoir membrane (intrusions), which are particularly advantageous as oviposition sites for certain arthropods. The invention is also directed to methods of making the arthropod diet delivery system wherein the protrusions are substantially simultaneously created and filled with diet. The diet delivery system is suitable for mass production of arthropods at a reasonable cost for uses including as biological control agents.

19 Claims, 3 Drawing Sheets

OTHER PUBLICATIONS

A. C. Cohen, D. A. Nordlund and R. A. Smith, "Mass Rearing of Entomophagous Insects and Predaceous Mites: Are the Bottlenecks Biological, Engineering, Economic, or Cultural?," *Biocontrol News and Information* (1991) 20 (3): 85N–90N.

A. N. Dahlan and G. Gordh, "Development of *Trichogramma Australicum* (Hym.: Trichogrammatidae) at Low and High Population Density in Artificial Diet," *Entomophaga* (1997) 42(4):525–536.

P. De Clercq and D. Degheele, "A Meat–Based Diet for Rearing the Predatory Stinkbugs Podisus Maculiventris and Podisus Sagitta [Het.: Pentatomidae]," *Entomophaga* (1992) 37(1):149–157.

P. De Clercq, F. Merlevede, and L. Tirry, "Unnatural Prey and Artificial Diets for Rearing *Podisus maculiventris* (Heteroptera: Pentatomidae)," *Biological Control* (1998) 12:137–142.

S.M. Greenberg, D.A. Nordlund, and Z. Wu, Influence of Rearing Host Adult Size and Ovipositional Behavior of Mass Produced Female *Trichogramma minutum* Riley and *Trichogramma pretiosum* Riley (Hymenoptera: Trichogrammatidae), *Biological Control* (1998) 11:43–48.

S. Grenier et al. "Potential for Mass Release of Insect Parasitoids and Predators through Development of Artificial Culture Techniques," In: *Pest Management in the Subtropics, Biological Control—a Florida Perspective,* Eds. D., Rosen, F. D. Bennett, and J. L. Capinera, Intercept Press, Andover, U.K., (1994) Chapter 10, pp. 181–205.

K.S. Hagen and R.L. Tassan, "A Method of Providing Artificial Diets to Chrysopa Larvae," *Journal of Economic Entomology* (1965) 58:999–1000.

D.A. Nordlund, Z.X. Wu and S.M. Greenberg, "In Vitro of *Trichogramma minutum* Riley (Hymenoptera: Trichogrammatidae) for Ten Generations, with Quality Assessment Comparisons of in Vitro and in Vivo Reared Adults," *Biological Control* (1997) 9:201–207.

J.L.D. Saavedra, J.C. Zanuncio, R.N.C. Guedes and P. De Clercq, "Continuous Rearing of *Podisus Nigrispinus* (Dallas) (Heteroptera: Pentatomidae) on and Artificial Diet," *Med. Fac. Landbouww. Univ. Gen.* (1996) 61(3a):767–772.

Z–N Xie et al., "In Vitro Culture of Trichogramma Spp. on Artificial Diets Containing Yeast Extract and Ultracentrifuged Chicken Egg Yolk but Devoid of Insect Components," *Biological Control* (1997) 8:107–110.

ARTHROPOD DIET DELIVERY SYSTEM

BACKGROUND OF THE INVENTION

1. Field of the Invention

The present invention relates to an improved arthropod diet packaging, presentation, and delivery system for the feeding or oviposition of arthropods. In particular, the invention is directed to an improved diet delivery system having a diet-filled reservoir covered with a stretchable membrane, wherein the reservoir further has diet-filled outwardly projecting protrusions formed in the stretchable membrane, which protrusions are in fluid communication with the reservoir. The invention is also directed to methods of making the diet delivery system of the invention. The arthropod diet delivery system is suitable for mass production of arthropods at a reasonable cost for uses including as biological control agents.

2. Description of the Art

Biological control is recognized as one of the best alternatives to the use of chemical insecticides for controlling insect pests. Use of beneficial arthropod predators and parasites for biological control on a large scale as an alternative to pesticides depends on the ability to mass produce large quantities of viable and biologically fit arthropods at a reasonable cost. Rearing of beneficial arthropods on their natural hosts/prey or on unnatural factitious hosts is too expensive to allow large scale use of beneficial arthropods in commercial agriculture. Accordingly, artificial diets or growth media and effective diet packaging/presentation/delivery systems are required for mass production at reasonable cost.

The Review Article by A. C. Cohen, D. A. Nordlund and R. A. Smith, "Mass Rearing of Entomophagous Insects and Predaceous Mites: Are the Bottlenecks Biological, Engineering, Economic, or Cultural?," *Biocontrol News and Information*, 20 (3): 85N–90N (1999) provides a detailed discussion of barriers to overcome in successful mass rearing of natural enemies. These include: development of nutritionally adequate artificial diets, suitable packaging for the diets, nondestructive handling of insects and mites, adequate moisture, prevention of microbial contamination of diet or insects living in close association prevention of loss of genetic fitness, adequate ventilation, appropriate thermal conditions, appropriate lighting, accommodation for moulting, oviposition sites, and accommodation for newly-closed first instars that are extremely vulnerable to desiccation and starvation.

High quality semi-solid artificial diets for mass rearing of arthropods at a reasonable cost have been described. U.S. Pat. Nos. 5,834,177 and 5,945,271 to Cohen describe semi-solid artificial diets for rearing entomophages (predatory arthropods and parasitic insects) which comprise a mixture of (a) cooked whole egg, (b) a protein-lipid paste (e.g., a mixture of ground beef and beef liver), and (c) a liquid, wherein the cooked whole egg forms a sticky, stringy substrate that keeps the mixture in stable form. The diet provides nutrients effective for supporting the growth of larvae of entomophages from the time of hatching until pupation and also provides nutrients effective for rearing entomophages which have predaceous adult stages. This diet parallels the texture and consistency of the insides of the natural prey, and is particularly suitable for rearing insect predators that pre-digest their prey and must recapture their digestive enzymes and ingest the digested, liquified medium to complete their digestion (extra-oral digestion). The diet may be used as a fresh semi-solid diet mixture or as a freeze-dried and reconstituted semi-solid diet. The diet may also be used as a supplement in the artificial diet for phytophagous (plant-eating) insects that supplement their plant-eating habits with insect consumption. Exemplary entomophages reared on the growth media include *Chrysoperla carnea* Stephens/Chrysopidac (lacewings); *Geocoris punctipes* (Say)/Lygaeidae (big eyed bug); *Serangium parcesetosum; Orius insidiosus*; and *Perillus bioculatus* and *Podisus maculiventris* (which are both predatory stink bugs in the family Pentatomidae).

A. C. Cohen and L. K. Smith (*Biological Control* 13:49–54 (1998)) report production of 15 continuous generations of green lacewings, *Chrysoperla rufilabris* Burmeister (Neuroptera: Chrysopidae), using the semi-solid diet of U.S. Pat. No. 5,834,177.

U.S. Pat. No. 6,235,528 B1 to Cohen describes semi-solid artificial diets or arthropods, including zoophagous arthropods and phytophagous arthropods including facultatively zoophagous phytophages. In one aspect, the growth medium is composed of a mixture of cooked egg, liquid, and carbohydrate source. In a second aspect, the growth medium is composed of a plant-based phytophage diet which includes cooked egg yolk or cooked whole egg. In a third aspect, the growth medium is composed of a mixture of cooked egg, liquid, and carbohydrate source in admixture with a plant-based phytophage diet which includes cooked egg yolk or cooked whole egg. The diets may be used as fresh or freeze-dried and reconstituted semi-solid diets. Exemplary arthropods fed on a selected diet included the entomophage *Chrysoperla rufilabris* (green lacewling) and *Lygus hesperus* Knight and *Lygus lineolaris* (facultatively zoophagous phytophages)

Semi-solid meat-based artificial diets have been described for rearing *Geocoris punctipes* (Say) in publications by A. C. Cohen, *Journal of Economic Entomology*, 78:1173–1175 (1985); A. C. Cohen and N. M. Urias, *The Southwestern Entomotologist*, 11:171–176 (1986); and A. C. Cohen and R. T. Staten in *Applications of Genetics to Arthropods of Biological Control Significance*, Eds. S. K. Narang et al., CRC Press, Inc., Chapter 7, pp. 121–132 (1994)). De Clercq et al. (*Entomophaga* 37:149–157 (1992) and Biological Control 12:137–142 (1998)) describe an artificial insect diet for rearing the predatory stinkbugs *Podisus maculiventris* and *Podisus sagitta* using the meat-based diet of Cohen (1985) with added fresh (raw, liquid) egg yolk. Saavedra et al. (*Med Fac Landbouww Univ Gent*61(3a):767–772 (1996) describe an artificial insect diet for *Podisus nigrispinus* based on the bovine meat diet developed by Cohen (1985, supra) having added bee's honey, brewer's yeast, fresh egg yolk, and Wesson's salt.

The problem of packaging an artificial arthropod diet is complicated by the need, in most cases, to maintain both moisture and a barrier to microbial attack while still keeping the diet accessible and phagostimulatory to the insects (Cohen et al., 1999, supra). Standard techniques for packaging diets for presentation and delivery to arthropods include packaging the diet in a membrane such as Parafilm® (a flexible, moldable self-sealing, odorless, moisture resistant, thermoplastic, semi-transparent, and practically colorless membrane). The packaged medium can be sterilized and will remain sterile for subsequent use for rearing the target arthropod.

The packaged diet can be presented to the arthropods in a shape and wall thickness that simulates natural prey. Cohen, 1985, supra, and Cohen and Urias, 1986, supra, report good production of larvae with a diet delivery system using a single layer of Parafilm® (stretched to 3-fold its normal width) wrapped around the meat-based semi-solid diet in cylindrical form and pressure-sealed along the longitudinal seam. Cohen and Staten, 1994, supra, report using flattened packets made of stretched Parafilm to contain the diet.

Cohen and Smith, 1998, supra, report feeding packets formed by sandwiching the semi-solid diet in two Parafilm® layers that were stretched to about three times their original length and width (i.e., as 45-micron-thick membranes). The membranes were sealed around the diet to form a flat sachet. U.S. Pat. No. 5,834,177 reports using Parafilm® stretched to about 15–20 microns thick.

Packaging of small volumes of liquid artificial diets in a thin membrane or coating using encapsulation or coating techniques, for use in rearing or oviposition of predators of harmful insects has been reported. In these methods, a capsule, a hemispherical well in a stretched membrane or other container for holding the liquid diet is formed and is subsequently filled with an aliquot of a liquid nutritive growth medium or liquid inducement medium. As necessary, air bubbles in the liquid are then removed, for example, with a syringe. The container is then sealed.

K. S. Hagen and R. L. Tassan (*Journal of Economic Entomology* 58:999–1000, 1965) describe a technique for producing paraffin-coated diet capsules to supply artificial liquid diet to Chrysopa larvae. A. C. Cohen (*Journal of Economic Entomology*, 76(4):957–959, 1983) describes improved methods for encapsulating small units of liquid suspension artificial diets in mixtures of waxes and plastic polymers, for rearing predators for use in biological control of insect pests. A. N. Dahlan and G. Gordh (*Entomophaga* 42(4):525–536, 1997) describe artificial eggs formed of an upper cover of clear polypropylene, 32–36 microns thick and a lower cover of clear polyethylene, 8–13 microns thick and covered with gelatine solution. Each egg was filled with 5–6 microliters of diet solution for development of *Trichogramma australicun* Girault.

Z.-H. Xie et al. (*Biological Control* 8:107–110, 1997) describe in vitro culture of Trichogramma spp. on artificial liquid diets contained in stretched plastic artificial eggs prepared with polyethylene film and coated with Elmer's School Glue (Borden, Inc., Columbus, Ohio) (20 microliters diet/stretched plastic artificial egg). D. A. Nordlund et al. (*Biological Control* 9:201–207, 1997) describe wax artificial eggs (WAEs) which consisted of liquid droplets of diet coated with a thin layer of paraffin-Vaseline® mixture (75%:25%) which were used to induce *Trichogramma minutum* Riley females to oviposit. S. M. Greenberg et al. (*Biological Control* 11:43–48, 1998) describe a study of the oviposition response of adult *Trichogramma minutum* Riley and *Trichogramma pretiosum* Riley females to wax artificial egg (WAEs) and stretched plastic artificial eggs (SPAEs) with 0.01% sodium bisulfite solution as an oviposition stimulant. The WAEs had a mean diameter of 3.2±0.03 mm. The SPAEs were prepared with a polypropylene film (22.9 microns thick) by impressing, by hand, the surface of the film with a 2-mm diameter and 1.5-mm high peg. The film was held, by vacuum, on a perforated metal female mold with 3.175-mm holes. After the SPEAs were formed (70 per 16 cm² area), the vacuum was released and the polypropylene film was removed and placed in the oviposition arena. The SPAEs were held convex side to the Tichogramma. The oviposition arena was then filled with oviposition stimulant. Any air bubbles that formed in the SPEAs were removed with a syringe.

J. E. Carpenter and P. D. Greany (*Biological Control* 11:203–208 (1998)) describe a liquid diet encapsulation method wherein Parafilm® was stretched bidirectionally to a final thickness of ca. 10–15 microns and applied to a template (made by drilling 24 1-cm diameter holes on 2-cm centers in a 4×6 pattern into a 1-cm aluminum plate). This plate was attached to a plenum, so that a vacuum could be applied after the Parafilm® was stretched over its surface. Hemisperical depressions (wells) were formed in the Parafilm® using a slight negative pressure (−5.0 cm mercury) along with mechanical distortion achieved by applying a probe slightly smaller in diameter than the hole in the template. The probe was pressed into the Parafilm®, stretching it to the near-breaking point, forming a well of about 0.5 ml in volume. The liquid medium was homogenized and strained through a wire mesh of ca. 2×2 mm, then pipetted into the wells, which were then sealed by applying a plastic film such as Handiwrap® to the surface of the template. A piece of aluminum foil was applied over the plastic wrap and a heated brass roller (ca. 170° C.) was used to heat seal the Parafilm® to the plastic wrap. The final encapsulated diet sheets resembled "bubble pak" used in packaging, that is, the individual wells of diet were surrounded by sealed film. U.S. Pat. No. 5,799,607 to Greany and Carpenter also describe this encapsulation procedure of a liquid medium.

U.S. Pat. No. 4,418,647 to Hoffman describes an artificial membrane having a curvilinear surface region, the outer surface of which is adapted to induce oviposition by adult Trichogramma wasps, and the inner concave surface of which defines a semi-enclosed cavity adapted for recovery of the oviposited eggs.

In the foregoing methods of packaging small volumes of artificial liquid diets in coated or encapsulated form for rearing or oviposition of insects, the container for the aliquot of liquid diet, e.g., well or capsule, was pre-formed and then filled with the liquid diet or inducement liquid in a separate subsequent step. Because liquids readily flow and seek their own level, the packaging of small volumes of liquid diets is relatively straight forward. The liquid diet will fill a container, filling in each nook and cranny. Air bubbles therein can be readily removed.

This is not true of semi-solid arthropod diets. Because of the thick, viscous properties of semi-solid arthropod diets, filling small volumes, e.g., less than about 0.5 cm diameter, has been heretofore impracticable. Presently, semi-solid diets are presented in larger volumes, e.g., diet packets of about 1×1×0.5 cm; 10.16×15.24×0.5 cm; 10.16×50.8×0.5 cm, which are covered or enclosed with a membrane. Covering the semi-solid diet with a thin membrane requires tedious stretching of the membrane by hand prior to enclosing the diet in the membrane. This time-consuming and labor intensive procedure of hand stretching of a membrane is not susceptible to automation, and because of the labor intensity, it adds to the cost of packaging arthropod diets.

As discussed above, artificial semi-solid arthropod diets have proven to be highly valuable for producing large numbers of viable and biologically fit arthropods for uses including as biological control agents. What is needed is an efficient system for packaging small volumes of a semi-solid arthropod diet in a stretched, thinned membrane.

BRIEF SUMMARY OF THE INVENTION

The present invention is directed to an improved system for the packaging, presentation, and delivery of a semi-solid arthropod diet, for the feeding or oviposition of arthropods, hereinafter denoted as arthropod diet delivery system. The arthropod diet delivery system of the invention comprises a diet-filled reservoir covered with a stretchable membrane, wherein the reservoir membrane has a plurality of arthropod feeding protrusions thereon which comprise stretched, thinned outwardly projecting areas in the stretchable membrane. The protrusions are filled with the semi-solid diet, and the interior of a protrusion is in fluid communication with the diet-filled reservoir.

The arthropod diet delivery system may optionally further include stretched, thinned inwardly protecting areas in the stretchable reservoir membrane, denoted as intrusions. The intrusions are particularly advantageous as oviposition sites for certain arthropods.

The invention is also directed to methods of making the arthropod diet delivery system wherein the protrusions are substantially simultaneously created and filled with diet. In these methods, the process of stretching the membrane to form protrusions and filling the protrusions comprise one step. These methods are amenable to scale-up and to automated packaging techniques. They are especially amenable to production of small, filled protrusions, which are difficult to attain by systems that are designed to fill pre-formed protrusions.

In brief, methods of making the arthropod diet delivery system of the invention comprise acting on a stretchable membrane which covers or encloses a reservoir of semi-solid arthropod diet with a protrusion-creating implement in a manner to create a plurality of stretched, thinned outwardly projecting areas in the reservoir membrane, denoted as protrusions, and to substantially simultaneously fill the protrusions with diet. Optionally, the implement may also create intrusions in the reservoir membrane. The result is a diet delivery packet having the desirable properties of selective thinning of the membrane material at the sites of potential feeding or oviposition, while protecting the diet from degradative exposure of the diet to the environment.

The semi-solid arthropod diet delivery system of the invention fulfills an important need for an effective diet packaging, presentation, and delivery system for efficient mass rearing of arthropods. Millions of arthropods are required for augmentative biological control and other biologically based technologies. Obtaining very large quantities of arthropods demands both (1) the use of inexpensive, highly nutritious diets which yield large numbers of viable and biologically fit arthropods at reasonable cost, such as the artificial semi-solid diets described above, and (2) an effective diet packaging, presentation, and delivery system for these artificial diets, which system is amenable to scale-up and to automated packaging techniques. The arthropod diet delivery system of the invention fulfills this need of providing an economical means for rearing arthropods. The invention also fulfills the need for large scale production of arthropods necessary for technologies such as augmentative biological control, sterile insect release, and production of pathogens and parasitic insects using mass-produced arthropods as food.

The present invention provides an efficient system for presenting arthropods with small volumes of semi-solid diet in a stretched, thinned membrane, e.g., protrusions, while avoiding the time-consuming and labor intensive procedure of hand stretching of a membrane. Additionally, because the diet within a protrusion is in fluid communication with the diet-filled reservoir, the invention diet delivery system provides arthropods with access to an abundance of diet medium.

Accordingly, it is an object of the invention to provide an improved system for the packaging, presentation, and delivery of semi-solid arthropod diet for the feeding or oviposition of arthropods and methods of producing the same.

Another object of the invention is the provision of an effective and economical diet delivery system for the large-scale production of arthropods.

A further object of the invention is the provision of a system for the packaging and delivery of semi-solid diets which system is amenable to scale-up and suitable for automated packaging techniques.

A still further object of the invention is to provide protection of arthropod diet from desiccation and microbial contamination.

Other objects and advantages of the invention will become readily apparent from the ensuing description.

DETAILED DESCRIPTION OF THE INVENTION

Definitions

Arthropods

Figure 1A:
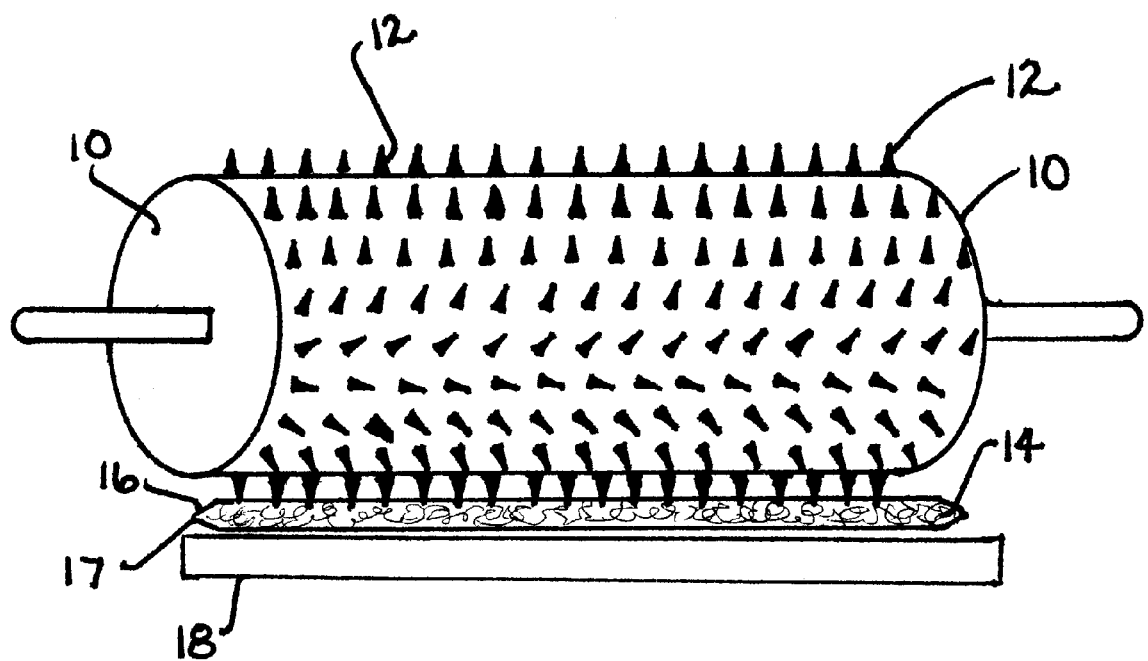
FIG. 1A is an isometric view showing a method of making the diet delivery system of the invention using a roller (10) having outwardly projecting pins (12). The pins act on a sandwich of semi-solid media (14) enclosed between two stretchable membranes (16, 17) and placed on a resilient pad (18).

The invention is designed for the presentation and delivery of semi-solid diet for the feeding or oviposition of arthropods. The phylum Arthropoda includes insects and arachnids. Within this phylum are zoophagous arthropods, phytophagous arthropods, and facultatively zoophagous phytophages. Of particular importance in this invention are those arthropods that are mass reared for subsequent release as biological control agents, for example, augmentative releases for control of populations of insect pests in commercial agriculture.

As used herein, the term "zoophagotis arthropods" refers to arthropods that consume animal materials, for example, insects that feed on other insects. Exemplary of zoophagous arthropods are predatory and parasitic insects such as entomophages, and arachnids such as spiders, mites or ticks.

As used herein, the term "entomophages" refers to predatory arthropods and parasitic insects (parasitoids). Entomophages are discussed in detail in the text *Entomophagous Insects* by C. P. Clausen, Hafner Publishing Company, New York (1972), which is incorporated herein by reference. Entomophage refers to insects that feed upon other insects. These insects are broadly divided into two general classes, predators and parasitic insects. While there are many instances of species that are intermediate between the two general classes, a parasitic insect, in general, refers to one that, in its larval stage, develops either internally or externally upon a single host individual, the latter eventually dying as a result. The adults are generally free-living, and their food sources are usually distinct from those of the larvae. In contrast, a predator is generally free-living in the larval stage also and requires a number of individuals to provide food to grow to maturity. Clausen, supra, reports that there are 224 families in 15 orders, which to some extent, feed upon other insects.

Entomophages of particular importance to commercial agriculture are those useful as biological control agents, for example, through augmentative releases, to control populations of insect pests on agricultural commodities. Without being limited thereto, exemplary of predatory arthropods having importance for biocontrol in a commercial agricultural setting include predators of the Order (species)/family: Heteroptera: *Geocoris punctipes* (Say)/Lygaeidae [big eyed bug]; *Podisus maculiventris* (Say)/Pentatomidae; *Podisus sagitta* (Fab.)/Pentatomidae; *Macrolophus caliginosus* Wagner/Miridac; Neuroptera: *Chrysoperita carnea* Stephens/Chrysopidae [lacewingas]; *Chrysopa sinica*/Chrysopidae; *Chrysopa scelestes* Banks/Chrysopidae; *Chrysopa lanata* lanata Banks/Chrysopidae; *Chrysopa septempunctata* Wesmaeal/Chrysopidae; Coleoptera: *Coleomegila maculata, Harmonia axyridis*/Coccinellidae, *Olla abdoiminalis*/Coccinellidae. Without being limited thereto, exemplary parasitoids having potential importance for biocontrol in a commercial agricultural setting include Hymenioptera, in particular, Trichogrammatidae; Braconidae, and Ichneumonidae; and Diptera, in particular, Tachinidae.

Exemplary zoophagous arachnids include mites (family Phytoseiidae), and spiders (families Lycosidae, Thomisidae, Linyphiidae, Araneidae).

As used herein, the term "phytophagous arthropods" refers to arthropods that consume plants. Without being limited thereto, exemplary of phytophlagous arthropods are Lepidoptera such as *Helicoverpa zea* (cotton bollworm), *Heliothis virescens* (tobacco budworm), *Spodoptera exigua* (beet armyworm) and other Spodoptera spp., *Trichoplusia ni* (cabbage looper), *Pseudoplusia includens* (soybean looper); Coleoptera such as Diabrotica spp., *Popillae japonica*, Epilachna spp.; various Curculionidae (weevils); Hemipteria/Heteroptera such as Lygus spp. (various Miridae), *Nezara viridula* (southern green stink bug), Eusehistus spp.; phytophagous mites (Tetranychidae); Diptera such as *Delia platura*.

As used herein, the term "facultatively zoophagous phytophages" refers to phytophagous (plant-eating) arthropods that display some animal material consumption in addition to eating plants. [See, A. C. Cohen, "Plant feeding by Predatory Heteroptera: Evolutionary and Adaptational Aspects of Trophic Switching," pp. 1–17, 1996, In: *Zoophagous Heteroptera: Implications for Life History and Integrated Pest Management*, O. Alomar and R. N. Wiedenmann, eds. Thomas Say Publications in Entomology, 1996, and A. C. Cohen, "Biochemical and Morphological Dynamics and Predatory Feeding Habits in Terrestrial Heteroptera," pp. 21–32, In: *Predatory Heteroptera in Agroecosystems: Their Ecology and Use in Biological Control*, M., Coll and J. R. Ruberson, eds., Thomas Say Publications in Entomology. Entomological Society of America, Lanham, Md., 1998.]

Without being limited hereto, exemplary of predominantly phytophagous insects that display some insect consumption in addition to eating plants, are Heteroptera: Miridae: Lygus spp., for example, *Lygus hesperus* Knight and *L. lineolaris*. Lygus spp. are known to be important pests in several cropping systems (seed alfalfa, cotton, strawberries, orchard crops). They are also known to supplement their plant-eating habits with some insect consumption. Mass rearing of phytophages is useful for other biocontrol purposes, for example to produce phytophage products such as entomopathic fungi or entomopathic viruses.

Semi-Solid Arthropod Diet or Growth Medium

As used herein, the term "semi-solid arthropod diet" refers to a diet or growth medium that has intermediate properties, especially in rigidity, between solids and liquids. A semi-solid diet has a degree of fluidity but substantially holds its shape and does not readily seek its own level in a container. Alternate descriptions of a semi-solid diet composition include slurry, gel, paste, viscous and slowly flowing slurry. The semi-solid artificial diet or growth medium is one which provides nutrients effective for rearing the target arthropod, that is, a diet or growth medium that provides nutrients in amounts and proportions effective to support growth of the target arthropods at the feeding site or supports oviposition at the oviposition sites, and preferably supports growth of larvae of the target arthropods so that they mature into pupae or adults. The diet may be used to feed a target adult arthropod that has a predaceous adult stage.

The semi-solid diet or growth medium should contain essential nutrients. Essential nutrients are defined as those nutrients such as minerals, amino acids, cholesterol, fatty acids, lipid soluble vitamins, and water soluble vitamins that are essential to the growth of the target arthropod. This can be readily determined for any circumstance. For instance, the basic nutritional requirements of parasitoids and predators for an artificial growth medium are discussed in S. Grenier et al. in *Pest Management in the Subtropics, Biological Control—a Florida Perspective*, Eds. D., Rosen, F. D. Bennett, and J. L. Capinera, Intercept Press, Andover, U.K., Chapter 10, pp. 181–205 (1994), which is incorporated herein by reference. As known to those in the art, nutrients essential for growth of an arthropod can vary among species. For any particular target arthropod, nutrients essential for growth can be determined by procedures known to those of skill in the art, for example, dietary deletion. The actual concentrations selected may be determined empirically by the practitioner skilled in the art.

Other adjuvants or supplements may also be incorporated into the medium to enhance the growth of the target arthropod, stimulate feeding, or prevent the growth of microbial contaminants.

Examples of semi-solid diet compositions meeting the criteria of providing nutrients for rearing of arthropods are described in U.S. Pat. Nos. 5,834,177; 5,945,271; 6,235,528 B1, and Cohen, 1985, supra. The texture, consistency, and composition of these growth media are well suited to the arthropods that pre-digest their food and must recapture their digestive enzymes and digested, liquified medium to complete their digestion (extra-oral digestion).

Stretchable Membrane

The stretchable membrane which covers or encloses the semi-solid diet must have the properties of stretchability, that is, flexibility, elasticity, pliability, and/or resiliency, and strength sufficient so that the membrane can be stretched and thinned beyond its modulus of elasticity to create a protrusion and intrusion without breaking the membrane.

The membrane may be formed from a variety of polymeric film-formers, including but not limited to paraffin, polyethylene, polypropylene, polyvinyl chloride, Parafilm® (a flexible, moldable, self-sealing, odorless, moisture resistant, thermoplastic, semi-transparent, and practically colorless membrane sold by American National Can™, Neenah, Wis. 54956), Whatman Laboratory Sealing Film (a self-sealing, heat resistant to 60° C., moisture proof, odorless, chemically resistant film which has high tensile strength and stretches in all directions, sold by Whatman), Handywrap®, Saranwrap®, waxed paper, polyethylene terephthalates (compound no. 7442, *The Merck Index*, 10$^{th}$ edition, Merck & Co., Inc. 1983; also see U.S. Pat. No. 2,465,319). Determination of other film-forming materials meeting the aforementioned criteria would be within the ambit of the skilled artisan.

The membrane which covers or encloses the semi-solid diet serves to protect the diet from degradative exposure of the diet to the environment. For example, it minimizes or prevents the diet from drying out or being accessed by microbes.

Preferred membranes for use in this invention are Parafilm® and Whatman Laboratory Sealing Film. Use of Parafilm® and Whatman Laboratory Sealing Film as a cover is particularly advantageous as these membranes may serve as a phagostimulant.

The Arthropod Diet Delivery System of the Invention

The arthropod diet delivery system of the invention is a means for packaging, presentation, and delivery of a semi-solid arthropod diet, which comprises a reservoir of semi-solid diet which is covered with a stretchable membrane, wherein the membrane has a plurality of arthropod feeding protrusions thereon, the interior of a protrusion being filled with the diet and being in fluid communication with the diet-filled reservoir. The diet delivery system may optionally further include intrusions in the stretchable membrane.

Key aspects of the arthropod diet delivery system of the invention include the following: (a) a plurality of stretched, thinned outwardly projecting areas in the reservoir membrane (protrusions) which are filled with the semi-solid arthropod diet; (b) fluid communication of the interior of a protrusion with the diet-filled reservoir; (c) optionally, stretched, thinned inwardly projecting areas in the reservoir membrane (intrusions).

A protrusion is a stretched, thinned area of the reservoir membrane that extends outwardly beyond the surface of the reservoir membrane surrounding the protrusion. A protrusion has a hollow interior with the interior of the protrusion being in fluid communication with the diet-filled reservoir such that diet in the reservoir is able to flow into a protrusion substantially simultaneously as a protrusion is created in the reservoir membrane. The diet in the protrusion is in fluid communication with the contiguous diet in the diet-filled reservoir.

Stretching of the stretchable membrane serves two functions: it reduces the thickness of the film through which the target arthropods must force their mouthparts to penetrate to feed on the diet, and it weakens the film, making it more readily penetrated by the mouthparts of the target arthropods. The mouthparts of typical predators (which generally are the smaller arthropods) must penetrate cuticles of both plants and insects that range from 5 to about 50 microns in thickness. The cuticles of plants and insects consist of a polysaccharide such as cellulose (plants) or chitin (insects), both of which materials are typically cross-linked with proteins via some type of bridging molecular connection. This produces a strong coating that is usually imbued or coated with waxes, which serve multiple functions, especially water-proofing. Some films, including, for example, Parafilm® and Whatman Laboratory Film, once stretched, mimic the natural cuticles of plants and insects and have been traditionally used as packaging for insect feeding and oviposition (egg insertion) sites. In addition, it must also be understood that the natural feeding mechanisms of arthropods with piercing and sucking mouthparts include the seeking of raised portions of their plant surfaces. Such raised places are characteristic of insect eggs, aphids, scale insects, or plant structures that are susceptible to feeding efforts. Thus, the arthropods are attracted to feed on non-flat surfaces, e.g., protrusions, and thus are attracted to feed on the diet delivery system of the invention.

A protrusion may have several shapes, including raised-convex, rounded, domed-shaped, elongated, conical, volcano-shaped, e.g., where the top or tip of the protrusion has collapsed inward. Alternative descriptions of a protrusion include protuberance, projection, bulge, convexity, nodule, nipple. The size and shape and thickness of a protrusion are described in detail, below, in the section entitled "Protrusion-Creating Method of the First Embodiment." As noted, above, the interior of a protrusion is in fluid communication with the diet-filled reservoir.

During the creation of a protrusion, the reservoir membrane is stretched to exceed the modulus of elasticity of the membrane, such that it will not return to its original shape prior to the stretching. The stretching is carried out so as not to perforate the membrane.

An intrusion is a stretched, thinned area of the reservoir membrane that extends inwardly below the surface of the reservoir membrane surrounding the intrusion. The diet in the intrusion is in fluid communication with the diet in the diet-filled reservoir.

An intrusion may be described by several terms, including depressed-concave, concavity, indentation, or dimple.

During the creation of an intrusion, the reservoir membrane is stretched to exceed the modulus of elasticity of the membrane, that is, the membrane is stretched such that it does not return to its original shape prior to the stretching. The stretching is carried out so as not to perforate the membrane.

The semi-solid diet or growth medium may be used in the diet delivery system of the invention in its fresh form or may be freeze-dried and used after reconstitution with liquid.

It is preferred that the semi-solid diet or growth medium used in the diet delivery system of the invention is substantially homogeneous. This minimizes or eliminates weeping of liquid in the semi-solid diet out of any opening in the membrane that may be created by the target arthropod as it pierces the membrane.with its mouthparts to feed on the diet.

Techniques for rearing arthropods in vitro on artificial diets have been described by Cohen et al., 1985, supra, which is incorporated herein by reference and in U.S. Pat. Nos. 5,834,177, and 5,945,271, which are incorporated herein by reference in their entirety. For example, eggs, larvae, nymphs or adults with predacious stages are provided with the growth medium in an amount effective to support growth, and incubated under conditions and for a period of time for the eggs or larvae to mature into pupae or adults, for nymphs to mature into adults and for the adults to advance through reproductive stages. Preferably, the growth medium is presented in a suitable container such as a petri dish, cage or multicell container. Organdy may be used to enclose cells to permit air flow and prevent escapes. Because of the mobility of first and second instar larvae of zoophagous arthropods and their predisposition for cannibalism in some species, multi-cell or other compartmentalized containers are preferred to segregate developing larvae.

The diet delivery system may be placed in any manner such that it is accessible to the target arthropods, including on the top of a cage, underneath a cage or inside a cage containing the target arthropods. Conveniently, plexiglass or other weight bearing material may be placed on the diet delivery system that is on top of the cage. Thus, when the mouthparts of a target arthropod penetrate and consume a portion of the diet, the weight bearing material puts hydraulic pressure on the diet to fill a gap created by the feeding of the target arthropod. Where the diet delivery system is placed underneath the cage, the weight bearing material may be placed on the top of the cage. In all cases, sufficient air flow to the target arthropods is maintained.

The invention is particularly advantageous for the packaging, presentation, and delivery of diet to arthropods for feeding or oviposition for the following reasons. (1) Arthropods are attracted to feed on non-flat surfaces, e.g., protrusions, and thus are attracted to feed on the diet delivery system of the invention. (2) The protrusions comprise stretched, thinned areas in the stretchable membrane, thus, arthropods can readily penetrate a protrusion with their mouthparts and feed. This feature is particularly important for presentation and delivery of diet to smaller arthropod predators. (3) The diet within a protrusion is in fluid communication with the diet-filled reservoir, thus, the invention provides arthropods with access to an abundance of diet medium. (4) The optional stretched, thinned, inwardly depressed areas in the membrane, e.g., intrusions, have the shape and membrane thickness that make them particularly conducive to oviposition therein by certain mature female arthropods. Because the membrane covering an intrusion is stretched and thinned, arthropod females can readily penetrate the membrane with their ovipositor and deposit eggs. Moreover, because the diet in the intrusion communicates with the diet in the reservoir, the larvae which hatch, and the other stages of the arthropod development, e.g., nymphs, pupae, adults, have access to a vast quantity of diet in the diet-filled reservoir. (5) The arthropod diet delivery system provides protection of the diet from desiccation and microbial contamination. (6) We have found that this simultaneous creation and filling of a protrusion minimizes or eliminates the creation of air pockets in the protrusion. (7) The diet delivery system of the invention provides a practical and an efficient means for packaging small volumes of a semi-solid arthropod diet in a stretched, thinned membrane.

Methods of Making the Arthropod Diet Delivery System of the Invention

The invention also includes methods of making the arthropod diet delivery system wherein the protrusions are substantially simultaneously created and filled with diet. These methods are amenable to scale-up and to automated packaging techniques.

In brief, methods of making the arthropod diet delivery system of the invention comprise acting on a stretchable membrane which covers or encloses a reservoir of semi-solid arthropod diet with a protrusion-creating implement in a manner to create a plurality of stretched, thinned outwardly projecting areas in the reservoir membrane, denoted as protrusions, and to substantially simultaneously fill the protrusions with diet. Optionally, the implement may also create a plurality of intrusions in the reservoir membrane.

Protrusion-Creating Method of the First Embodiment

The method of First Embodiment for making the arthropod diet delivery system of the invention which comprises a diet-filled reservoir covered with a stretchable membrane, wherein the membrane has a plurality of stretched, thinned outwardly projecting areas in the membrane, denoted as protrusions, the interior of a protrusion being filled with diet and being in fluid communication with the diet-filled reservoir, comprises:

(1) contacting a stretchable membrane which covers or encloses a reservoir of semi-solid arthropod diet with a retractable protrusion-creating implement to stretch the membrane sufficient to exceed the modulus of elasticity of the membrane in the area of contact without perforating the membrane to thereby create a plurality of stretched, thinned inwardly projecting areas in the reservoir membrane and (2) retracting the implement;

wherein sufficient friction exists between the stretched membrane and the implement so that, when the implement is retracted, the stretched membrane adheres to the implement, to invert the inwardly projected areas and form the protrusions; and wherein the interior of a protrusion is in fluid communication with the diet-filled reservoir and wherein the diet-filled reservoir has sufficient negative pressure such that as a protrusion is created due to the retraction of the implement, it is substantially simultaneously filled with diet. Optionally, the implement may also create intrusions.

Retractable Protrusion-Creating Implement of the Method of the First Embodiment

Any protrusion-creating implement that can act upon the surface of the stretchable membrane so as to stretch the membrane sufficient to exceed the modulus of elasticity in the area of contact without perforating the membrane and which has friction with the stretched membrane sufficient to cause the stretched membrane to become inverted when the implement is retracted is encompassed by this method.

Figure 1B:
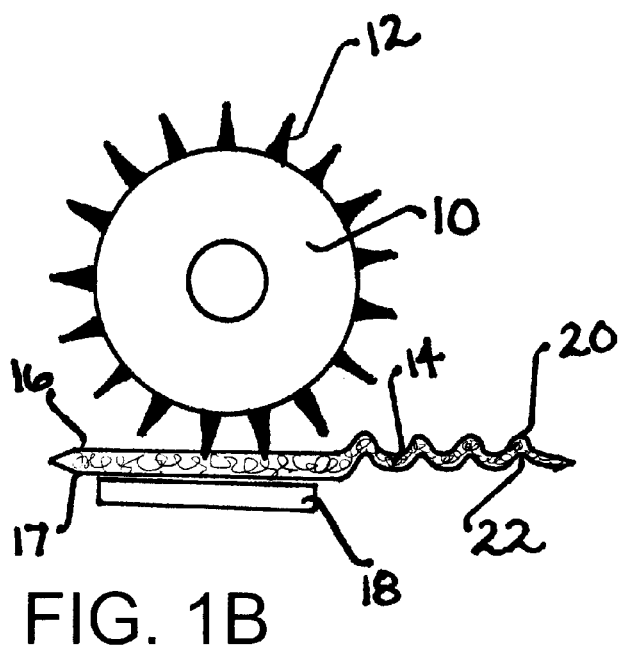
FIG. 1B is a cut away side view. When the roller (10) is rolled over the sandwich of semi-solid media (14) which is enclosed between stretchable membranes 16 and 17, the pins 12 stretch the membranes beyond their modulus of elasticity, and when the roller continues to roll, the pins are retracted, thereby causing the stretched areas of the stretchable membranes to invert and to form diet-filled protrusions 20 in membrane 16 and to form intrusions 22 in membrane 17.

A preferred implement for making protrusions in this method is a device which can efficiently make a plurality of protrusions, for example, an implement which has a plurality of protrusion-creating members so that a plurality of areas on the membrane are stretched and are inverted when the members are retracted. This includes, for example, a protrusion-creating implement having a base element and a plurality of outwardly extending members attached to the base. Examples include a die with multiple outwardly extending members which can be pressed into or rolled over the reservoir membrane and retracted to create multiple protrusions during the pressing or rolling of the implement. An exemplary implement is shown in FIGS. 1A and 1B and is described in the Example, below. The outwardly extending members have a shape, size, and dimension such that when they are pressed or rolled or otherwise caused to act on the membrane, they stretch the membrane beyond its modulus of elasticity at the point of action on the membrane, but do not puncture or perforate the membrane. The coefficient of friction between an outwardly extending member and the stretched membrane is such that when the member is retracted, the stretched membrane adheres to the retracting member sufficient to be drawn outwardly beyond the surface of the reservoir membrane to form a protrusion. That is, when the protrusion-creating device is retracted, the stretched, thinned area created by an outwardly extending member is inverted to create a protrusion having a hollow interior. The interior of a protrusion is in fluid communication with the diet-filled reservoir such that as a protrusion is created due to the retraction of the implement, it is substantially simultaneously filled with the diet. We have found that this simultaneous creation and filling of a protrusion minimizes or eliminates the creation of air pockets in the protrusion. Air pockets in the diet in a protrusion are disadvantageous because they increase the likelihood of spoilage of diet due to oxidation of nutrients, microbial spoilage by aerobic microorganisms, desiccation of the diet, and discouragement of feeding by arthropods, which would encounter air, rather than their targeted diet.

Examples of outwardly extending members include members that are long and narrow such as needles, pins, pegs, nails, dowels, rods, spindles, spikes, and the like; members that are v-shaped such as pipet tips, spikes, hollow cylinders such as glass micropipets or stainless steel liquid chromatography injection syringes. The outwardly extending member has the property that it can stretch the membrane beyond the modulus of elasticity without perforating the membrane. In some instances, it may be desirable to blunt the tip of an outwardly extending member to assure that perforation of the membrane does not occur during stretching. The implement may be made out of any suitable material that has the required strength and has the required coefficient of friction with the stretched membrane. These include for example, metal, glass, plastic and the like.

Selection of the shape of the outwardly extending member of the protrusions-creating implement is determined by the size, shape, and volume of protrusions desired to be created and filled. Selection of a particular protrusion-creating device meeting the aforementioned criteria would be within the ambit of the skilled artisan.

As used herein, the term "exceed the modulus of elasticity" means that the membrane is acted on with force or pressure sufficient to stretch the membrane and mechanically change its shape such that when the force or pressure is removed, the stretched membrane area will not return to its original unstretched shape, that is, an area in the membrane is created that is permanently stretched.

As used herein, the term "sufficient friction" between the retractable protrusion-creating implement and the stretched membrane means that the surface property of the implement in the area of contact with the membrane and the surface property of the stretched membrane are such that when the implement is retracted, the stretched membrane adheres to the implement sufficient to invert the inwardly projecting areas and form protrusions. A surface property of the membrane which may contribute to friction is the "stickiness" of the membrane, e.g., self-sealing membranes. It is not necessary that every stretched, thinned inwardly projecting area be inverted, as these intrusions have the shape and membrane thickness that make them particularly conducive to oviposition therein by certain mature female arthropods.

As used herein, the recitation of the phrase "the interior of a protrusion is in fluid communication with the diet-filled reservoir" means that the diet in the reservoir is able to flow into a protrusion.

As used herein, the phrase "sufficient negative pressure" when used to describe the diet-filled reservoir means that when a protrusion is created the diet is drawn from the reservoir into the protrusion. The energy of the stretching and inversion of the stretched membrane may also contribute to the flow of the diet from the reservoir into a protrusion.

As used here, the phrase "substantially simultaneously" means that as a protrusion is formed, it is filled with diet.

The size, shape, length and width, and volume of a protrusion and the thickness or thinness of the stretched, thinned areas which make up a protrusion can be controlled by factors, including the size and shape of the outwardly projecting member of the protrusion-creating implement; the pressure used in creating the protrusion; the depth and speed at which the protrusions are created; the membrane material; the temperature of the membrane material; the viscosity and elasticity of the diet; the thickness of a diet sandwich, the composition of the resilient pad, and the coefficient of friction between the stretched membrane and protrusion-creating implement. The effect of any parameter on the size, shape, length and width, or volume of a protrusion in a particular set of circumstances can be determined by routine experimentation.

It is not necessary that every stretched, thinned inwardly projecting area be inverted, as these intrusions have the shape and membrane thickness that make them particularly conducive to oviposition therein by mature female arthropods. The number of protrusions for a particular circumstance can be determined by the practitioner. It is preferred that at least about 50%, preferably at least about 75%, more preferably at least about 90%, and even more preferably at least about 95% of the stretched, thinned areas created when the implement acts on the stretchable membrane to exceed its modulus of elasticity adhere sufficiently to the implement such that when the implement is retracted protrusions are created and filled. The dimensions and numbers of protrusions per unit area are selected based on (a) the biology of the target arthropod, e.g., the size of the arthropod, the reach of its mouth parts, the type of mouth parts, e.g., single stylet, tong-shaped, the stage in the life cycle of the arthropod, e.g., whether it's a newly hatched larvae, or first, second or third instar; (b) whether or not the arthropods are housed in individual cages or communally; (c) whether a protrusion or protrusions are to feed the target arthropod through a life cycle without adding additional diet delivery systems of the invention.

The diameter of a feeding site protrusion is generally in the range of about 20–10,000 microns, and the height is generally in the range of about 15–25,000 microns. The desired size depends on the size of the target arthropod. It is desirable to have at least 1 protrusion/cm$^2$ to 100 protrusions/cm$^2$. The number can vary depending on the size of the protrusion and size of the target arthropod.

For large arthropods, that is, arthropods greater than about 500 mg, which arthropods generally have extended reach of their mouthparts, the diameter of a feeding site protrusion is generally in the range of about 500 to 10,000 microns, and the height is generally in the range of about 10,000 to 25,000 microns, although large arthropods could feed on smaller sized protrusions. If fed in individual cells, 1 feeding site protrusion/cell may be sufficient because the larger arthropod, after feeding on the diet in the protrusion, can readily access the diet in the reservoir contiguous to the diet in the protrusion. However, more than one feeding site protrusion/cell may be a more efficient feeding approach. In the case where the target arthropod is fed communally, it is desirable to provide the arthropods with diet packets having a plurality of protrusions/diet packet/number of packets/communal feeding cage that is effective for rearing the target arthropods.

For intermediate-sized arthropods, that is, arthropods of about 10 to 500 mg, the diameter of a feeding site protrusion is generally in the range of about 200 to 500 microns, more preferably in the range of about 200 to less than about 500 micron diameter, and the height is generally in the range of about 300 to 10,000 microns, although intermediate-sized arthropods can feed on smaller or larger sized protrusions.

For smaller arthropods, that is, arthropods of less than about 10–12 mg, the diameter of a feeding site protrusion is preferredly generally in the range of about 20 to 200 microns, and the height is preferredly generally in the range of about 15 to 300 microns, although protrusions may also be used which are larger. For smaller arthropods such as the lacewing that are reared individually, for example in Verticel® (multicell container made of cardboard) cells (ca. 4×6×12 mm or about a 400 $\mu$l capacity), it is generally desirable to have 2 or 3 to about 10 feeding site protrusions/cell depending on the size of the protrusion and the stage of the lacewings development. Again, where the target arthropod is fed communally, food packets are provided with the number of protrusions/packet/cage which provides diet effective for rearing the arthropods in the cage.

The optimum feeding site protrusion number and dimensions to rear a target arthropod under a particular set of circumstances can readily be determined by routine experimentation.

It is preferred, particularly, where insects are reared in individual cells that the protrusions are approximately evenly positioned throughout the arthropod diet delivery system so that there is approximately even distribution of protrusions to accommodate the target arthropod in each cell, and provide effective feeding.

The thickness of the stretched, thinned membrane of the protrusions is selected so that it is penetrable by the mouthpart of the target arthropod. The thickness of the stretched, thinned membrane of the protrusion is generally in the range of about 1–200 microns. For large arthropods, the thickness of the membrane of a feeding site protrusion is generally in the range of about 10 to 200 microns. For intermediate-sized arthropods, the thickness of the membrane of a feeding site protrusion is generally in the range of about 5 to 150 microns. For smaller arthropods, the thickness of a feeding site protrusion is generally in the range of about 1 to 50 microns.

The stretched, thinned areas are useful as oviposition sites. The size, shape, length and width, and volume of an intrusion and the thickness or thinness of the stretched, thinned areas which make up an intrusion can be controlled by factors, including the shape of the protrusion-creating implement; the pressure used in creating the intrusion; the membrane material; the temperature of the membrane material; the elasticity and viscosity of the diet, the thickness of the diet sandwich, the composition of the resilient pad, and the coefficient of friction between the stretched membrane and protrusion-creating implement. The effect of any parameter on the size, shape, length and volume of an intrusion or the thickness or thinness of the stretched, thinned areas in a particular set of circumstances can be determined by routine experimentation.

An exemplary way to make the arthropod diet delivery system of this embodiment is to sandwich the semi-solid media between two layers of a protective material to form a diet reservoir, wherein at least one layer is a stretchable membrane that has a coefficient of friction with the protrusion-creating implement so as to substantially adhere to the implement when it is retracted so as to form a diet-filled outwardly projecting protrusion.

In one embodiment, the other protective layer may comprise a non-stretchable material, e.g., glass, hard plastic petri dish or other non-stretchable cover or container. In this case, protrusions are created and filled only in the stretchable membrane.

Figure 2A:
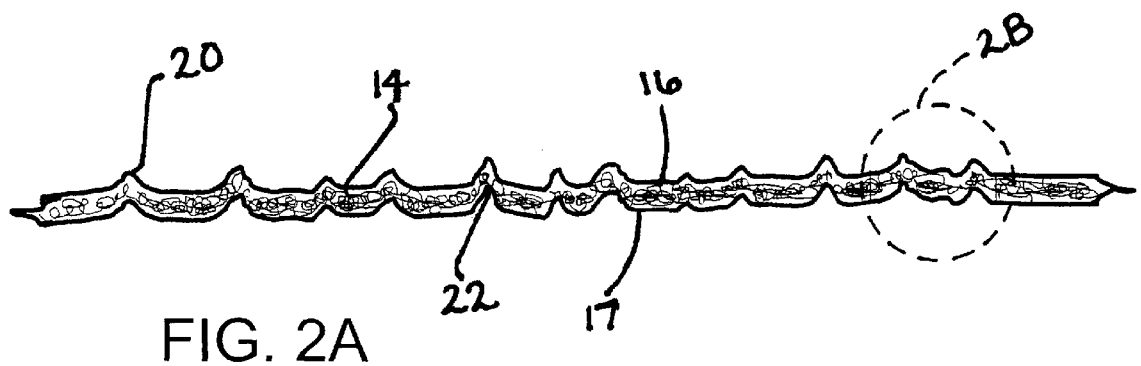
FIG. 2A show the arthropod diet delivery system of the invention. The reservoir of semi-solid diet 14 is covered with stretchable membranes 16 and 17. Diet-filled protrusions 20 in membrane 16 are in fluid communication with the diet-filled reservoir. Membrane 17 has intrusions 22.
Figure 2B:
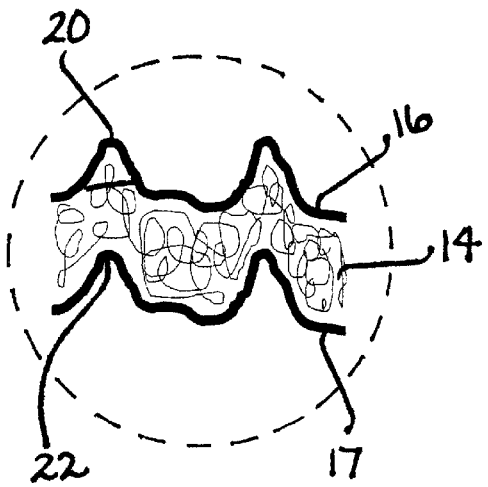
FIG. 2B is an enlarged view of the arthropod diet delivery system shown in FIG. 2A.

In another embodiment, both layers are of the diet sandwich reservoir are made of a stretchable membrane having the required coefficient of friction with the implement. The diet sandwich is contacted with the protrusion-creating implement to stretch one or both membranes beyond their modulus of elasticity. When the protrusion-creating device is retracted, the stretched, thinned areas of the layer or layers that are stretched by the implement are inverted. The stretched, thinned areas on the membrane that are directly contacted by the implement, denoted as the first membrane, upon retraction of the implement, form outwardly projecting hollow protrusions which are substantially simultaneously filled with diet as described above. But this same action, the stretched, thinned areas of the second stretchable membrane is drawn inward into the diet sandwich when the implement is retracted to thereby form stretched, thinned, inwardly depressed areas (intrusions). This is due to the transfer of force of the implement through the first membrane as it is stretched and through the diet sandwich to the second membrane that is stretched. An intrusion so formed is substantially opposite the protrusion formed when an outwardly projecting member on the protrusion-creating implement is retracted, as shown in FIGS. 2A and 2B.

In all of the variations of the method, the result is an arthropod diet delivery system having the desirable properties of selective thinning of the membranes to create sites of potential feeding or oviposition, while protecting the diet from degradative exposure to the environment.

The method of making the arthropod diet delivery system of the invention is amenable to scale-up and automation. For example, an exemplary protrusion-creating implement is a roller having outwardly projecting members as discussed above. As a practical matter, a resilient or pliable surface, e.g., a rubber pad or foam covered roller, is situated underneath the area of the diet sandwich impacted by the protrusion-creating implement. This facilitates creation of the stretched, thinned areas by the implement and minimizes or eliminates puncturing of the stretchable membrane. The roller may be rolled one or more passes, depending on the number of outwardly extending members and the number of protrusions to be created.

FIGS. 1A and 1B show a method of making the diet delivery system of the invention using roller 10 having outwardly projecting pins 12. The pins act on a reservoir of semi-solid media 14 sandwiched between stretchable membranes 16 and 17. The diet sandwich is placed on resilient rubber pad 18. When roller 10 is rolled over the diet sandwich, pins 12 stretch the membranes beyond their modulus of elasticity, and when the roller continues to roll, the pins are retracted, thereby causing the stretched areas of the stretchable membranes to invert and to form diet-filled protrusions 20 in membrane 16 and to form intrusions 22 in membrane 17. The arthropod diet delivery system of the invention is shown further in FIGS. 2A and 2B. As can be seen from the drawings, the diet-filled protrusions 20 in membrane 16 are in fluid communication with the diet-filled reservoir, and are substantially opposite intrusions 22 in member 17. An exemplary roller is described in the Example, below.

Another exemplary protrusion-creating implement is a base element having at least one flat surface wherein outwardly projecting members are attached to the flat surface.

This implement can be pressed, e.g., by hydraulic pressure, into the diet sandwich reservoir and retracted to create and fill a plurality of protrusions, and optionally form intrusions. Again, as a practical matter, the diet reservoir in the area impacted by the protrusion-creating implement, is placed on a resilient surface to avoid perforation of the stretchable membrane by the implement. It is preferred that the outwardly projecting members be of uniform length and enter the diet sandwich reservoir with uniform pressure.

Protrusion-Creating Method of the Second Embodiment

The method of Second Embodiment for making the arthropod diet delivery system of the invention which comprises a diet-filled reservoir covered with a stretchable membrane, wherein the membrane has a plurality of stretched, thinned outwardly projecting areas in the membrane, denoted as protrusions, the interior of a protrusion being filled with diet and being in fluid communication with the diet-filled reservoir, comprises:

(1) contacting a stretchable membrane which covers or encloses a reservoir of semi-solid arthropod diet with a retractable protrusion-creating implement to stretch the membrane sufficient to exceed the modulus of elasticity of the membrane in the area of contact without perforating the membrane to thereby create a plurality of stretched, thinned outwardly projecting protrusions in the reservoir membrane, and (2) retracting the implement;

wherein minimal friction exists between the stretched membrane and the implement so that, when the implement is retracted, the stretched membrane remains projecting outward; and wherein the interior of a protrusion is in fluid communication with the diet-filled reservoir and wherein as a protrusion is created, it is substantially simultaneously filled with diet. The implement may also create intrusions.

An exemplary way to make the arthropod diet delivery system of this embodiment is to sandwich the semi-solid media between two layers of a stretchable membrane wherein there is minimal friction between the membranes and the protrusion-creating implement. The diet sandwich is contacted with the protrusion-creating, implement to stretch both membranes beyond their modulus of elasticity, thereby creating thinned, stretched inwardly projecting areas (intrusions) in the membrane that is directly contacted with the implement and thinned, stretched outwardly projecting areas (protrusions) in the second membrane. Because there is minimal or no friction between the protrusion-creating implement and the diet reservoir membrane, the intrusions and protrusions do not invert when the implement is retracted. The protrusions are filled with diet substantially simultaneously as they are created.

A preferred implement for making protrusions in this method is a device which can efficiently make a plurality of protrusions, for example, an implement which has a plurality of protrusion-creating members so that a plurality of areas on the membrane are stretched, as described in detail in the method of the First Embodiment, except that there is minimal friction between the implement and the stretchable membrane, so that the stretched, thinned areas of the membrane do not adhere to the implement and do not become inverted as the implement is retracted. Exemplary of implements that have minimal coefficient of friction are those made of Teflon® (synthetic resinous fluorine-containing polymers). Alternatively, the membrane is selected to have a minimal coefficient of friction with a protrusion-creating implement so that the stretched, thinned areas of the membrane do not invert when the implement is retracted. In all circumstance, the implement and membrane have minimal friction such that the protrusion is created and filled during positive mechanical pressure of the implement on the membrane.

Implements for use in this embodiment include the following: a protrusion-creating implement having a base clement and a plurality of outwardly extending members attached to the base. Another exemplary protrusion-creating implement is a base clement having at least one flat surface wherein outwardly projecting members are attached to the flat surface. This implement can be pressed, e.g., by hydraulic pressure, into the diet sandwich reservoir to create and fill a plurality of protrusions and then retracted. As a practical matter, the diet reservoir in the area impacted by the protrusion-creating implement, is placed on a resilient surface to avoid perforation of the stretchable membrane by the implement. It is preferred that the outwardly projecting members be of uniform length and enter the diet sandwich reservoir with uniform pressure.

The dimensions and numbers of protrusions and intrusions are as described above in the method of the First Embodiment.

The method of making the arthropod diet delivery system of the invention is amenable to scale-up and automation.

Protrusion-Creating Method of the Third Embodiment

The method of Third Embodiment for making the arthropod diet delivery system of the invention which comprises a diet-filled reservoir covered with a stretchable membrane, wherein the membrane has a plurality of stretched, thinned outwardly projecting areas in the membrane, denoted as protrusions, the interior of a protrusion being filled with diet and being in fluid communication with the diet-filled reservoir, comprises:

contacting a stretchable membrane which covers or encloses a reservoir of semi-solid arthropod diet with a protrusion-creating implement which applies negative pressure for a time and pressure sufficient to stretch the membrane sufficient to exceed the modulus of elasticity of the membrane in the area of contact without perforating the membrane to thereby create a plurality of stretched, thinned outwardly projecting protrusions in the reservoir membrane, wherein the interior of a protrusion is in fluid communication with the diet-filled reservoir and wherein as a protrusion is created due to the negative pressure, it is substantially simultaneously filled with diet.

Figure 3A:
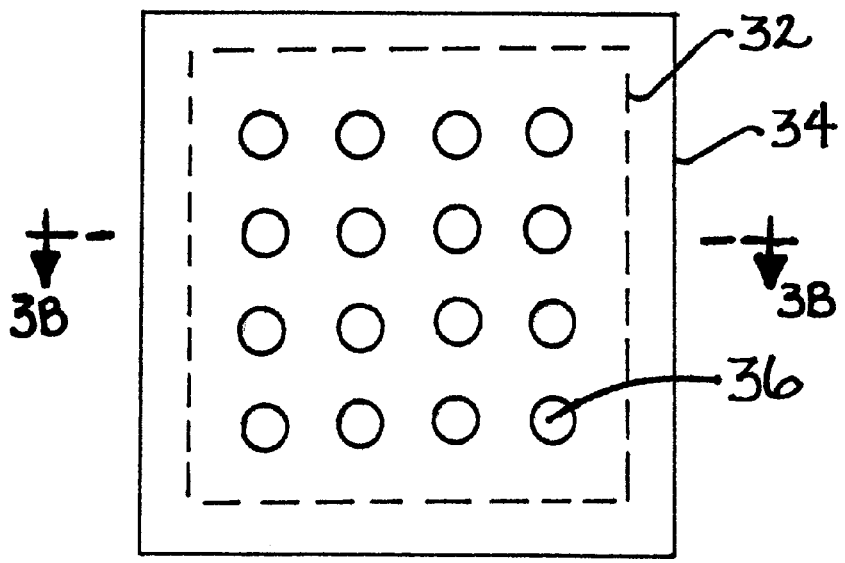
FIG. 3A is a top view and FIG. 3B is a side view (cross section) showing a method of making the diet delivery system of the invention using negative pressure. The protrusion-creating implement (30) has base element 32 connected to plate 34 (having holes 36) and in vacuum communication therewith. Base element 32 also has a vacuum attachment means (38) to communicate with a means for applying a negative pressure. Membrane-covered diet reservoir, shown in FIG. 3B as a sandwich of semi-solid media 14 enclosed between two stretchable membranes (16, 17), is placed on plate 34 and in vacuum communication with holes 36 to allow an applied vacuum to be exerted on the membranes to create protrusions 20 in membrane 16 and intrusions 22 in membrane 17.
Figure 3B:
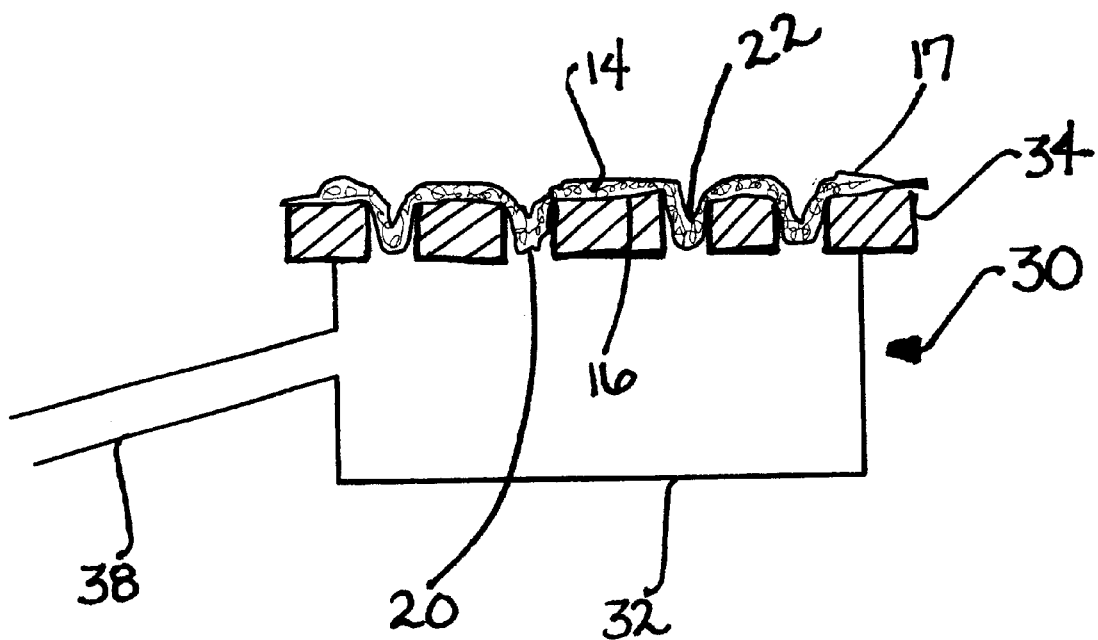

In the method of the Third Embodiment of making the arthropod diet delivery system of the invention, the protrusions are substantially simultaneously created and filled using negative pressure (a vacuum). The protrusion-creating implement for this embodiment comprises a hollow base element and a means for creating protrusions when the protrusion-creating, implement is placed in vacuum communication with the membrane-covered diet reservoir and subjected to negative pressure. An exemplary protrusion-creating implement is shown in FIGS. 3A and 3B. The protrusion-creating implement is shown as 30 in FIG. 3B which has base element 32 connected to plate 34 (having holes 36) and in vacuum communication therewith. Base clement 32 also has a vacuum attachment means (38) to communicate with a means for applying a negative pressure, e.g., a vacuum line or vacuum pump. A membrane-covered diet reservoir, shown in FIG. 3B as a sandwich of semi-solid media 14 enclosed between stretchable membranes 16 and 17, is placed on plate 34 and in vacuum communication with holes 36 to allow an applied vacuum to be exerted on membrane 16 or membranes 16 and 17. A negative pressure (vacuum) is applied to protrusion-creating implement 30 for a time and pressure to stretch diet reservoir membrane 16 beyond the modulus of elasticity without breaking the film to thereby create protrusions and to substantially simultaneously fill the protrusions with the semi-solid arthropod diet to obtain filled protrusions 20 shown in FIG. 3B. Optionally, negative pressure is applied also stretch membrane 17 to create intrusions 22 therein.

The protrusion-creating implement can be made of any suitable material that can hold a negative pressure, e.g., stainless steel, aluminum, plastic. An alternative means to plate 34 having holes 36 is a plate having hollow tubes outwardly extending therefrom and in vacuum communication with element 32 to allow an applied vacuum to be exerted on membrane 16 or membranes 16 and 17. The tubes are in vacuum communication with the base element 32 to allow an applied negative pressure to be exerted on the membrane-covered diet reservoir. It may be desirable to have a gasket between base element 32 and plate 34 or to use vacuum grease to assure a seal between element 32 and plate 34 as known in the art.

The size of protrusion-creating members of the implement, e.g., holes in the plate or hollow tubes outwardly extending from the plate, are selected based on the desired number, and size of protrusions for the target arthropod, as discussed in detail above. Exemplary hole or tube openings are generally in the range of about 0.5 mm to 5 mm diameter. Also as discussed in detail above, the membrane should have a combination of stretchability and strength such that it can be stretched beyond the modulus of elasticity to the desired size (volume) without breaking or perforating and will be a desired thickness that will be penetrable by the arthropods.

The dimensions and numbers of protrusions and intrusions are as described above in the method of the First Embodiment.

This method is amenable to scale-up and automation.

Protrusion-Creating Method of the Fourth Embodiment

The method of Fourth Embodiment for making the arthropod diet delivery system invention which comprises a diet-filled reservoir covered with a stretchable membrane, the membrane has a plurality of stretched, thinned outwardly projecting areas in the membrane, denoted as protrusions, the interior of a protrusion being filled with diet and being in fluid communication with the diet-filled reservoir, comprises:

contacting a stretchable membrane which covers or encloses a reservoir of semi-solid arthropod diet with a protrusion-creating implement which applies positive pressure for a time and pressure sufficient to stretch the membrane sufficient to exceed the modulus of elasticity of the membrane in the area of contact without perforating the membrane to thereby create a plurality of stretched, thinned outwardly projecting protrusions in the reservoir wherein the interior of a protrusion is in fluid communication with the diet-filled reservoir and wherein as a protrusion is created due to the positive pressure, it is substantially simultaneously filled with diet.

In the method of the Fourth Embodiment of making the arthropod diet delivery system of the invention, the protrusions are substantially simultaneously created and filled using positive pressure. The protrusion-creating implement for this embodiment comprises a hollow base element and a means for creating protrusions when the protrusion-creating implement is connected to the membrane-covered diet reservoir and subjected to positive pressure e.g., positive air pressure. These could be, for example, holes in the base member or hollow tubes outwardly extending from the base member and in communication therewith, for example a positive pressure manifold. The base member also has an attachment means to communicate with a means for applying a positive pressure, e.g., a positive pressure pump, to the protrusion-creating implement, and allow an applied pressure to be exerted on the membrane that is located adjacent to the means for creating protrusions. A positive pressure is applied to the protrusion-creating implement for a time and pressure to stretch the diet reservoir membrane beyond the modulus of elasticity without breaking the film to thereby create protrusions and to substantially simultaneously fill the protrusions with the semi-solid arthropod diet.

The protrusion-creating implement can be made of any suitable material that can hold a positive pressure, e.g., stainless steel, aluminum, plastic. The size of protrusion-creating members of the implement, e.g., holes or hollow tubes, are selected based on the desired number, and size of protrusions for the target arthropod, as discussed in detail above. Also as discussed in detail above, the membrane should have a combination of stretchability and strength such that it can be stretched beyond the modulus of elasticity to the desired size (volume) without breaking or perforating and will be a desired thickness that will be penetrable by the arthropods.

The dimensions and numbers of protrusions and intrusions are as described above in the method of the First Embodiment.

This method is amenable to scale-up and automation.

EXAMPLE

The following example is intended only to further illustrate the invention and is not intended to limit the scope of the invention which is defined by the claims.

This example presents data comparing the arthropod diet delivery system of the invention with conventional diet packets. This example also provides data showing that the invention diet delivery system can be used for fresh semi-solid diet and freeze-dried, reconstituted semi-solid diet.

Materials and Methods

For these experiments, 10×10×0.5 cm diet packets were made by making a diet "sandwich" between two layers of Parafilm®. About 20 g of the semi-solid arthropod diet described in U.S. Pat. No. 5,834,177 and Cohen and Smith, 1998, supra, or freeze-dried, reconstituted (with water) semi-solid arthropod diet as described in U.S. Pat. No. 5,945,271, were dispensed inside the packets with a cake decorating tool.

The Invention diet delivery packets were prepared in accordance with the method of the First Embodiment as follows: Each diet packet sandwich as described above was flattened so that diet was evenly spread within the packet, and the packet was placed on a resilient surface (made from the underside of a rubber mouse pad). Each packet was then rolled with a roller made of cast aluminum and having outwardly extending pins made of stainless steel. The roller was 35 mm in diameter and 250 mm in length. The pins were 6 mm in height and had a 2 mm diameter at the base. The spacing of the pins was 6 mm.

When a packet was rolled with the roller, the pins, upon contact with the diet packet, stretched the upper membrane sufficient to exceed the modulus of elasticity of the membrane in the area of contact without perforating the membrane to thereby create a plurality of stretched, thinned inwardly projecting areas in the upper stretchable membrane and stretched the lower membrane sufficient to exceed the modulus of elasticity of the membrane in the area of contract without perforating the membrane to create a plurality of stretched, thinned outwardly projecting areas in the lower stretchable membrane. Upon retraction, the friction of the pins and the stretched membranes caused the stretched membranes to adhere to the pins sufficient to invert the inwardly projected areas to form protrusions and simultaneously fill the so-formed protrusions with diet. The retraction of the pins also inverted the outwardly projecting areas to form intrusions. An intrusion so formed was substantially opposite the protrusion formed by the same pin. Packets were rolled repeatedly with the roller being offset to increase the frequency of the filled protrusions to between 5–20 protrusions per 25 $mm^2$ feeding unit. The mean of the range of the diameter of the filled protrusions was 641.5000 microns; standard error of diameter=32.2353. The mean of the range of the height of the protrusions was 327.1000 microns; standard error of height=18.2717.

The Control packets of diet were made as described by Cohen and Smith, 1998, supra, wherein the Parafilm® was hand stretched so that the original 0.125 mm thickness of the film is reduced to about 0.025–0.050 mm thickness. This was clone by stretching the Parafilm® to about three times its original length and width by stretching it first in one direction and stretching again in the direction 90 degrees from the initial stretch.

Feeding units for testing the invention packets were formed by gluing organdy (organza) cloth onto both flat sides of Verticel®, as described by Cohen and Smith, 1998, supra. The packets were placed on top of the Verticel® feeding units and were pressed against the cells, which contained individual lacewing larvae. Additional pressure was applied constantly by placing a piece of Plexiglass on top of the diet packet, which was on top of the feeding unit. This pressure helped assure that possible warps or distortions in the feeding packet would not pull the feeding surface away from the insects.

The Control feeding packets were tested in parallel with the invention packets using the feeding units prepared as described above for the invention packets.

Results of experiments reported in Table 1 are from trials replicated 5 times where Control packets versus the Invention packets were provided to *Chyrsoperla rufilabris* caged in Verticel® feeding units that were 10 cm×10 cm. Adults were harvested from these feeding units and allowed to produce eggs in their standard adult cages made from 3 gallon ice cream cartons topped with organdy cloth. Adults were fed their standard diet, and eggs were harvested and counted as described by Cohen and Smith, 1998, supra.

In a group of parallel experiments (see Table 2), two different diets were compared, freeze-dried, reconstituted (FD) and fresh (F), using the diet delivery system of the invention. In these experiments, the number of eggs per day produced by adults derived from larvae reared on freeze-dried versus fresh diet packaged in the diet delivery system of the invention were compared.

Table 1 shows the results of the study comparing the invention diet delivery system and the convention diet packet using hand stretched Parafilm®. As can be seen from the data, the mean number of eggs per day were not significantly different in a paired T test between the packet treatments. This data documents that using the invention diet delivery system is as effective in producing arthropods as the conventional system using hand stretched membrane, while avoiding the labor intensive and time consuming step of hand stretching the membrane. Since it can take about 1/50 th less time (even less if automated) to make the invention diet delivery packets compared to the hand stretched packets, time and labor costs are reduced using the diet delivery system of the invention.

Table 2 shows that both types of diet (freeze-dried and fresh) produced equal fecundity reflecting that the adults derived from larvae that were reared on diet from the invention diet delivery system were able to get complete nutrition and a fully complete amount of the diet from packet protrusions of the diet delivery system of the invention.

TABLE 1

Number of eggs per day over 5 days of oviposition by fully mature adults derived from larvae fed the semi-solid diet presented in the Control packet versus the diet delivery system of the invention.

| Packet type | Mean (+/− std. error) |
|---|---|
| Control | 26.7 (2.88) |
| Invention | 27.7 (2.24) |

TABLE 2

Number of eggs per day produced by adults derived from larvae reared on freeze-dried versus fresh diet packaged in the diet delivery system of the invention. Each mean represents 5 replications of each treatment consisting of adults that emerged from feeding cells in a 10 × 10 cm feeding unit.

| Day after adult eclosion | Fresh diet (+/− std. error) | Freeze-dried diet (+/− std. error) |
|---|---|---|
| 1 | 8.0 (1.27) | 10.3 (2.39) |
| 2 | 21.6 (2/83) | 23.2 (3.61) |
| 3 | 29.4 (2.08) | 32.8 (3.88) |
| 4 | 38.4 (4.48) | 36.8 (2.23) |
| 5 | 42.6 (3.86) | 35.5 (2.67) |

It is understood that the foregoing detailed description is given merely by way of illustration and that modification and variations may be made within, without departing from the spirit and scope of the invention. All publications and patents cited herein are hereby incorporated by reference in their entirety.

What is claimed is:

1. An arthropod diet delivery system, which comprises a reservoir of semi-solid diet which is covered with a stretchable membrane, wherein the reservoir membrane has a plurality of arthropod feeding protrusions thereon which comprise stretched, thinned outwardly projecting areas in the stretchable membrane which are filled with the semi-solid diet, wherein said protrusions have a diameter of less than about 0.5 cm, and wherein the interior of a protrusion is in fluid communication with the diet-filled reservoir wherein the reservoir membrane further includes a plurality of intrusions therein which comprise strectched, thinned inwardly projecting areas in the strechable membrane.

2. The diet delivery system of claim 1 wherein the diet reservoir comprises a diet sandwich wherein the semi-solid media is enclosed between a first protective material and a second protective material, wherein at least one of the protective materials is a stretchable membrane, and wherein the stretchable membrane has diet-filled protrusions thereon.

3. The diet delivery system of claim 2 wherein both of the first and second protective materials comprise stretchable membranes, and wherein at least one of the stretchable membranes has diet-filled protrusions thereon.

4. The diet delivery system of claim 3, wherein said first stretchable membrane has diet-filled protrusions thereon and where said second stretchable membrane includes a plurality of intrusions therein which comprise stretched, thinned inwardly projecting areas in the stretchable membrane.

5. The diet delivery system of claim 1 wherein said protrusions have a diameter of less than about 673 microns.

6. The diet delivery system of claim 1 wherein said protrusions have a diameter of less than about 500 microns.

7. The diet delivery system of claim 1 wherein said protrusions have a diameter of less than about 200 microns.

8. The diet delivery system of claim 1 wherein said protrusions have shapes selected from the group consisting of raised-convex, rounded, domed-shaped, elongated, conical, and volcano-shaped.

9. The diet delivery system of claim 1 wherein said protrusions have a height of less than about 10,000 microns.

10. The diet delivery system of claim 1 wherein said protrusions have a height of less than about 300 microns.

11. The diet delivery system of claim 2 wherein said protrusions in said at least one stretchable membrane are at least about $1/cm^2$ membrane.

12. The diet delivery system of claim 2 wherein said protrusions in said at least one stretchable membrane are less than about $100/cm^2$ membrane.

13. The diet delivery system of claim 2 wherein said protrusions in said at least one stretchable membrane are about 5–20 protrusions per 25 $mm^2$ membrane.

14. A method of making an arthropod diet delivery system which comprises a diet-filled reservoir covered with a stretchable membrane, wherein the membrane has a plurality of protrusions thereon which comprise stretched, thinned outwardly projecting areas in the membrane, the interior of a protrusion being filled with diet and being in fluid communication with the diet-filled reservoir, the method comprising:

acting on the stretchable reservoir membrane with a protrusion-creating implement to form a plurality of protrusions and to substantially simultaneously fill the protrusions with diet, wherein the interior of a protrusion is in fluid communication with the diet-filled reservoir.

15. The method of claim 14 wherein the protrusion-creating implement also forms a plurality of intrusions in the membrane.

16. The method of claim 14 wherein acting on the stretchable membrane comprises:

(1) contacting a stretchable membrane which covers or encloses a reservoir of semi-solid arthropod diet with a retractable protrusion-creating implement to stretch the membrane sufficient to exceed the modulus of elasticity of the membrane in the area of contact without perforating the membrane to thereby create a plurality of stretched, thinned inwardly projecting areas in the reservoir membrane, and (2) retracting the implement;

wherein sufficient friction exists between the stretched membrane and the implement so that, when the implement is retracted, the stretched membrane adheres to the implement, to invert the inwardly projected areas and form the protrusions; and wherein the interior of a protrusion is in fluid communication with the diet-filled reservoir and wherein the diet-filled reservoir has sufficient negative pressure such that as a protrusion is created due to the retraction of the implement, it is substantially simultaneously filled with diet.

17. The method of claim 14 wherein acting on the stretchable membrane comprises:

(1) contacting a stretchable membrane which covers or encloses a reservoir of semi-solid arthropod diet with a retractable protrusion-creating implement to stretch the membrane sufficient to exceed the modulus of elasticity of the membrane in the area of contact without perforating the membrane to thereby create a plurality of stretched, thinned outwardly projecting protrusions in the reservoir membrane, and (2) retracting the implement;

wherein minimal friction exists between the stretched membrane and the implement so that, when the implement is retracted, the stretched membrane remains projecting outward; and wherein the interior of a protrusion is in fluid communication with the diet-filled reservoir and wherein as a protrusion is created, it is substantially simultaneously filled with diet.

18. The method of claim 14 wherein acting on the stretchable membrane comprises:

contacting a stretchable membrane which covers or encloses a reservoir of semi-solid arthropod diet with a protrusion-creating, implement which applies negative pressure for a time and pressure sufficient to stretch the membrane sufficient to exceed the modulus of elasticity of the membrane in the area of contact without perforating the membrane to thereby create a plurality of stretched, thinned outwardly projecting protrusions in the reservoir membrane, wherein the interior of a protrusion is in fluid communication with the diet-filled reservoir and wherein as a protrusion is created due to the negative pressure, it is substantially simultaneously filled with diet.

19. The method of claim 14 wherein acting on the stretchable membrane comprises:

contacting a stretchable membrane which covers or encloses a reservoir of semi-solid arthropod diet with a protrusion-creating implement which applies positive pressure for a time and pressure sufficient to stretch the membrane sufficient to exceed the modulus of elasticity of the membrane in the area of contact without perforating the membrane to thereby create a plurality of stretched, thinned outwardly projecting protrusions in the reservoir membrane, wherein the interior of a protrusion is in fluid communication with the diet-filled reservoir and wherein as a protrusion is created due to the positive pressure, it is substantially simultaneously filled with diet.

* * * * *